United States Patent [19]

Denard

[11] Patent Number: 5,364,378
[45] Date of Patent: Nov. 15, 1994

[54] ANTI-BACK FLOW BAG FOR WASTE

[76] Inventor: Ruthie Denard, 74 Garfield, No. 305, Detroit, Mich. 48201

[21] Appl. No.: 86,244

[22] Filed: Jul. 1, 1993

[51] Int. Cl.$^5$ ............................................... A61F 5/44
[52] U.S. Cl. .................................... 604/335; 604/332; 604/345
[58] Field of Search .................................. 604/332–345

[56] References Cited

U.S. PATENT DOCUMENTS

| | | |
|---|---|---|
| 2,496,175 | 7/1950 | Perry . |
| 2,815,025 | 12/1957 | Fenton ........................ 604/335 |
| 3,523,534 | 8/1970 | Nolan . |
| 3,780,739 | 12/1973 | Frank . |
| 4,233,977 | 11/1980 | Mattson . |
| 4,294,252 | 10/1981 | Einset . |
| 4,387,713 | 7/1983 | Calanni . |
| 4,604,095 | 8/1986 | Samuelsen . |
| 4,973,323 | 11/1990 | Kaczmarek et al. ............ 604/332 |

*Primary Examiner*—Randall L. Green
*Assistant Examiner*—Rob Clarke
*Attorney, Agent, or Firm*—Dykema Gossett

[57] ABSTRACT

A unique colostomy or ileostomy bag includes an anti-back flow member provided by a thin plastic tube. The structure of the thin plastic tube reduces any likelihood of waste contacting a patient's skin. The thin plastic tube has a relatively large opening compared to a seal positioned adjacent the patient. Thus, any waste passing through the seal tends not to contact the thin plastic member adjacent an entrance to the thin plastic member. Rather, the waste contacts the thin plastic member at a downstream position. At the downstream position, any waste on the thin plastic member would not be adjacent to patient, and would tend to not contact the patient. The thin plastic member has relatively little rigidity such that it presents little resistant to flow of the waste material between the sides of the thin plastic member. In this way, the waste moves easily between the sides of the thin plastic member and into a bag for storage. In further features of the invention, belt loops are positioned on each side of the bag to assist in carrying the bag on a patient. Further, various structures for rolling and securing the bag such that the bag may be periodically opened for removable of waste are also disclosed.

1 Claim, 3 Drawing Sheets

ANTI-BACK FLOW BAG FOR WASTE

BACKGROUND OF THE INVENTION

This application in general relates to a bag for waste which has a unique anti-back flow structure.

In the prior art, colostomy bags and ileostomy bags are utilized for patients who have had the portion of their intestines surgically bypassed such that wastes exit through a opening in their body called a stoma. Patients utilizing such devices are often subject to extreme discomfort since the wastes often contact the skin in the area of the stoma. The waste products are aggravating to the skin since they will contain fecal matter, or possibly digestive juices.

Prior art bags have attempted to prevent contact between the waste matter and the skin in the area of the stoma by utilizing various types of check valves which prevent back flow of the waste through the opening in the bag. The known structures for achieving these goals have not been entirely successful, however, and it would be desirable to develop an improved bag which would significantly reduce any contact between the waste matter and the skin in the area of the stoma.

The prior art check valves have typically utilized relatively rigid materials. Such relatively rigid check valves do not open easily to allow passage of waste materials, sometimes resulting in waste materials remaining in the area of an opening to the check valve. This is undesirable, as it increases the chances of the waste material contacting the patient. Further, the prior art check valves and colostomy bags have sometimes included restrictions in the flow passage from the stoma into the check valve. This is undesirable as it will sometimes lead to waste materials remaining in the area of the opening to the check valve, which is adjacent to the patient. This is undesirable.

SUMMARY OF THE INVENTION

In a disclosed embodiment of the present invention, a colostomy bag incorporates a seal which contacts the stoma, and a surrounding patch which further protects the skin in the area of the stoma. A bag is attached to the patch on the side of the patch removed from the patient. Within the bag, a thin plastic tube surrounds an opening in the seal, and has an inner diameter which is greater than the inner diameter of the seal opening. Thus, any waste passing through the seal would tend to pass into the opening in the thin plastic tube, and would not contact the thin plastic tube in the area adjacent the opening. Rather, the wastes pass into the thin plastic tube, and are pulled downwardly by gravity. The thin plastic tube has two thin plastic sides which move away from each other, to allow passage of the waste material into the body of the bag. The thin plastic sides, having been wetted by previously passing waste materials, adhere to each other and prevent back flow of the waste into the tube.

The tube has an opening which is larger than the opening in the seal, and further since the tube is formed of thin plastic sides, there is not a tendency for the waste materials to build up in the area of the opening. Thus, the waste materials are not only prevented from backing up towards the opening, but are also moved away from the opening such that there is a reduced chance of any of such materials contacting the patient.

In a further feature of the present invention belt loops are formed on each side of tho patch. The belt loops assist in supporting the bag on the patient.

These and other features of the present invention can be best understood from the following specifications and drawings, of which the following is a brief description.

DETAILED DESCRIPTION OF A PREFERRED EMBODIMENT

Figure 1:
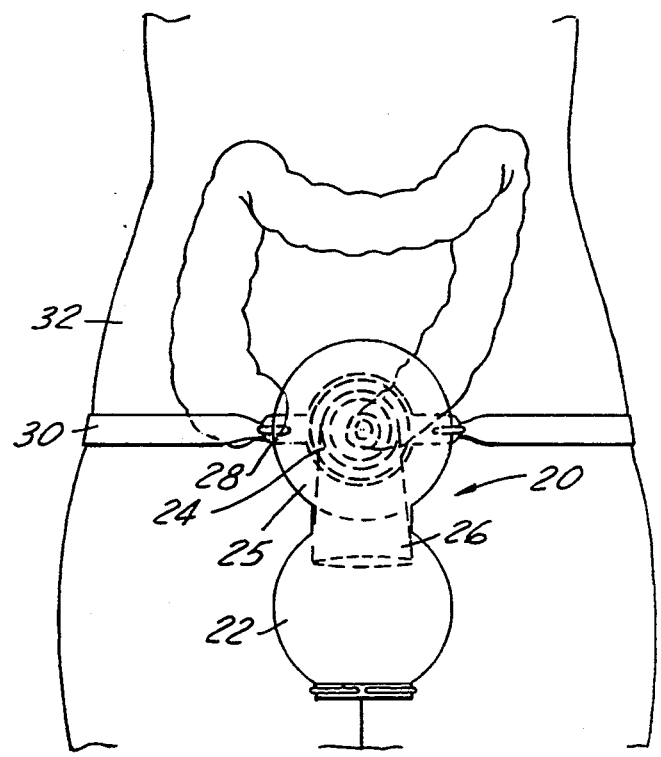
FIG. 1 is a front view showing a colostomy bag on a patient.

Colostomy bag 20 is illustrated in FIG. 1 including a bag structure 22, a seal 24 contacting the patient 32, a patch 25 contacting the patient's skin, and an anti-back flow thin plastic tube 26 received within bag 22. As shown, belt loops 28 are positioned on each side of the bag 22, and receive a belt 30 to support the bag 20 on a patient 32.

Figure 2:
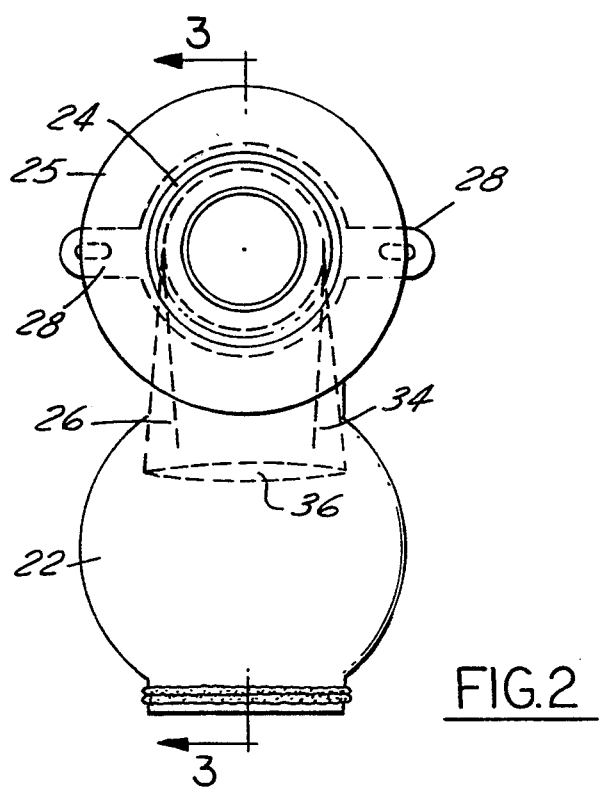
FIG. 2 is another front view of the bag illustrated in FIG. 1 but on a larger scale.

As shown in FIG. 2, thin plastic tube 26 consist of two thin plastic members 34 and 36. The plastic tube 26 is preferably formed of thin plastic material that has little or no rigidity, and which moves easily apart to allow passage of waste material therethrough under the influence of gravity. The thin plastic material adheres together against back flow of waste material back into the tube 26.

Figure 3:
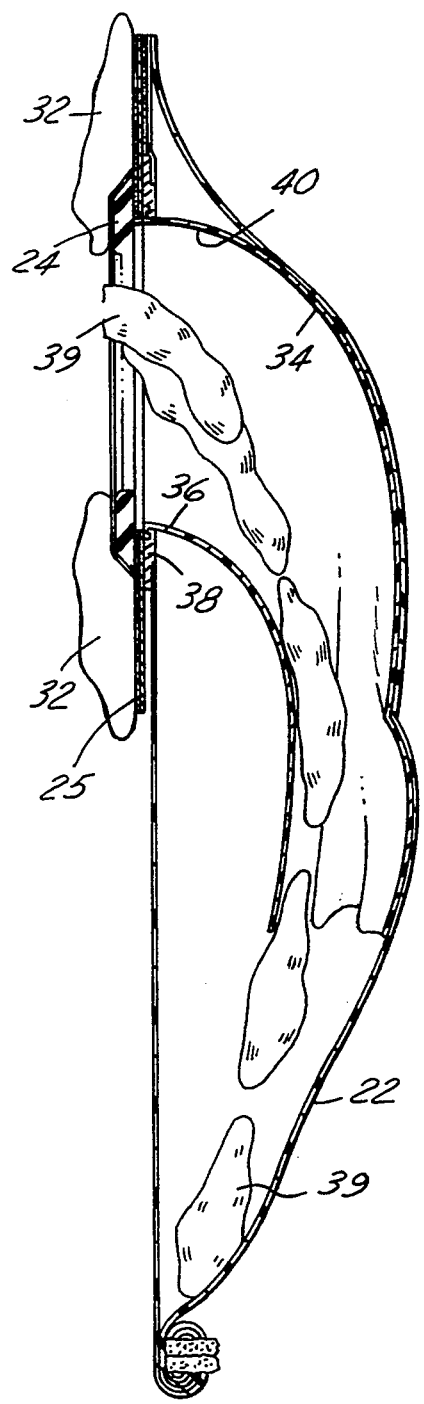
FIG. 3 is a cross-sectional view taken along line 3—3 of FIG. 2.

As shown in FIG. 3, the seal 24 is positioned adjacent to the patient 32. Patch 25 contacts the skin, and may receive an adhesive to assist in securing bag 22 to the patient 32. A spacer member 38 is positioned between the patch 25 and bag 22. Spacer member 38 adds rigidity to the opening to the tube 26. This improves the ability of the bag to keep the waste from the patient 32. As shown, thin plastic tube 26 has sides 34 and 36, with an opening 26 positioned concentric to the opening in seal 24, but having a greater inner diameter then the inner diameter of seal 24. As shogun, when waste material 39 moves through an opening 40 in the thin plastic tube 26, it tends to not contact either side 34 or 36 in the area adjacent the opening 40. Since the sides 34 and 36 are formed of thin plastic, the force of gravity pulling the waste 39 downwardly allows the waste material to move between the two sides 34 and 36 and fall into the bag 22.

Figure 4:
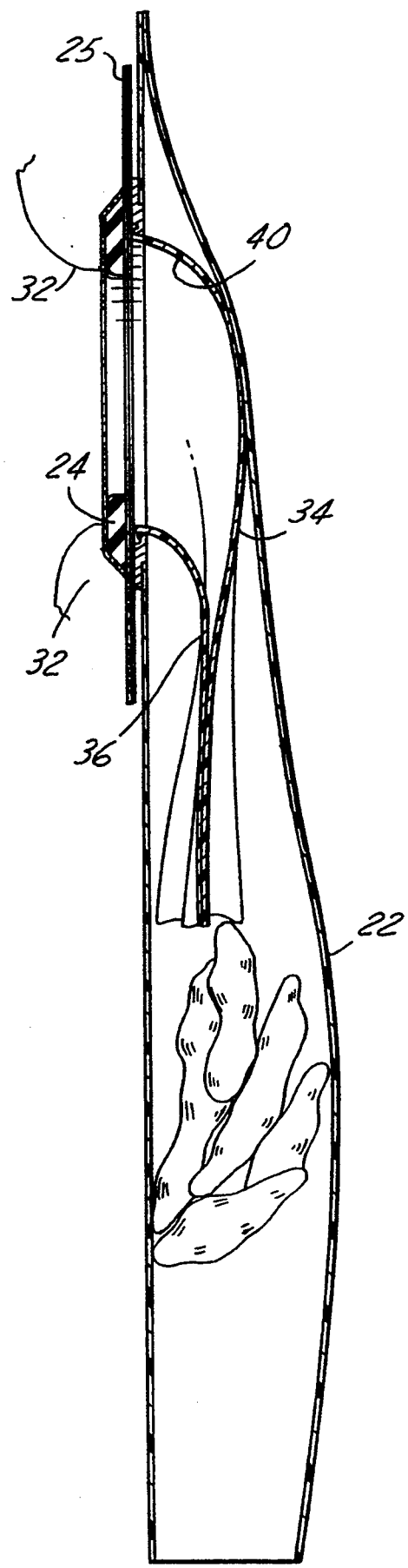
FIG. 4 is a sectional view similar to FIG. 3, but showing a subsequent step in the use of the inventive colostomy bag.

As shown in FIG. 4, after the waste has fallen into the bag 22, the sides 34 and 36 tend to adhere together at a position spaced from opening 40. The waste materials are now removed from seal 24, opening 40, and thus there is a reduced likelihood that any of the waste would contact patient 32, causing irritation to the skin of the patient.

The benefits of this invention are in large part due to the fact that the thin plastic tube 26 is formed of thin plastic film with little rigidity or elasticity such that it adheres together easily, and yet moves away from the two sides 34 and 36 easily when waste is positioned between the two sides, and gravity is pulling the waste downwardly. Further, since the entrance 40 to the thin plastic tube 26 is of a greater internal diameter than the opening in seal 24, it is unlikely that any waste will contact the thin plastic tube 26 in an area adjacent to the patient 32. Rather, the initial contact between thin plastic tube 26 and the waste material 39 tends to be further downstream. In this way, there is less likelihood that any waste will contact the patient's skin.

Figure 5:
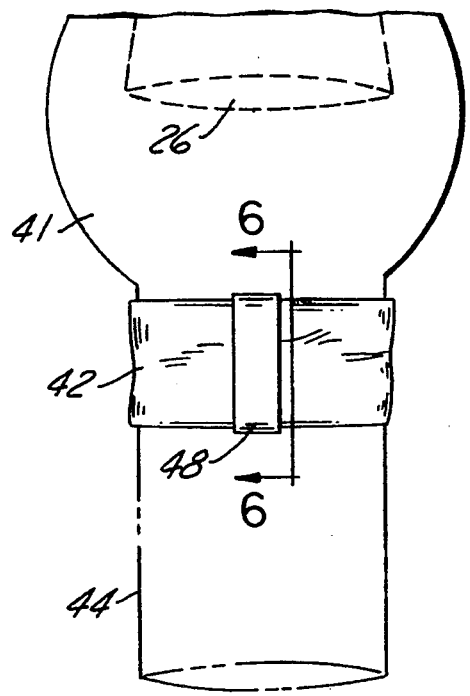
FIG. 5 is a fragmentary front view of another embodiment of the colostomy bag.

FIG. 5 shows a bag 41, which has a bottom 42 which is rolled upwardly from a position 44. In this embodiment, the bag may be opened at its bottom to the position shown in phantom at FIG. 4 to allow drainage from the bag. As show, 1, a securing member 48 may secure the bag 41 at this location.

Figure 6:
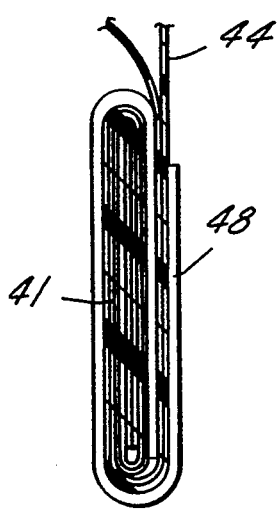
FIG. 6 is a cross-sectional view taken along line 6—6 of FIG. 5.

As shown in FIG. 6, securing member 48 may be bent around the rolled up bag 41 to secure see in the position shown in FIG. 5.

Figure 7:
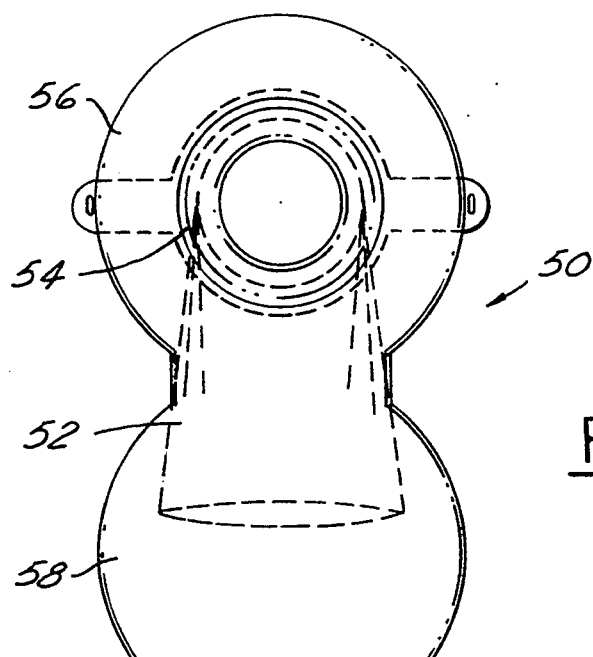
FIG. 7 is a view of still another embodiment of this invention.

FIG. 7 shows yet another bag embodiment 50 having a thin plastic tube 52, with a seal 54, a patch 56, and a storage portion 58. An end portion 60 is utilized and is rolled to a closed position.

Figure 8:
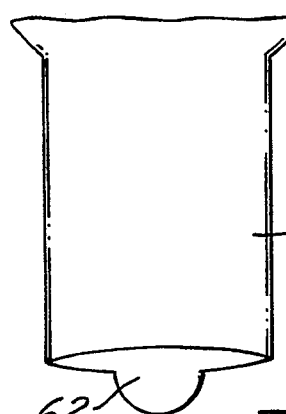
FIG. 8 is a view of a bottom portion of the embodiment illustrated in FIG. 7.

As shown in FIG. 8, a tab member 62 at the bottom of rolled portion 60 assist in rolling of the bag 50.

Figure 9:
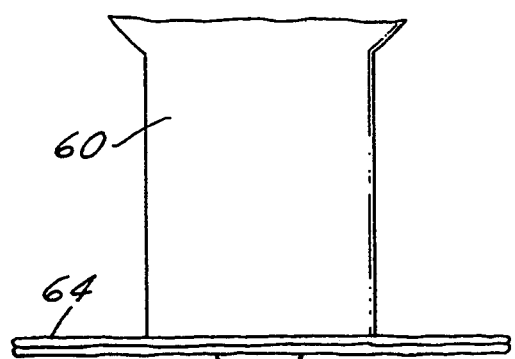
FIG. 9 is a view similar to FIG. 8 but showing another feature of the embodiment.

As further shown in FIG. 9, closure member 60, which may be of a structure 64 such as a pipe cleaner or a twist tie closure, is positioned at the end of roll portion 60.

Figure 11:
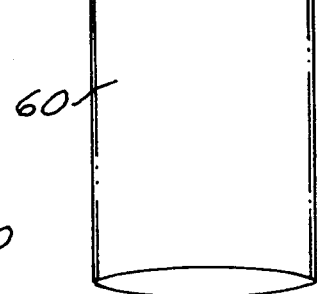
FIG. 11 illustrates a view subsequent to the view showing in FIG. 10.
Figure 10:
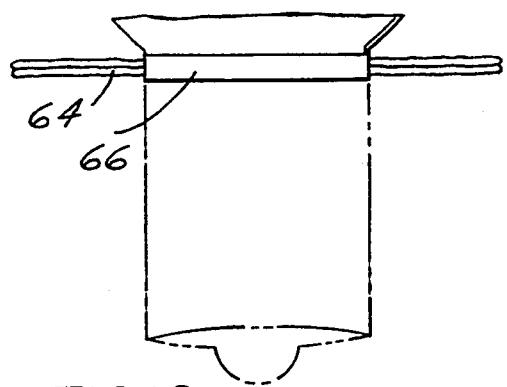
FIG. 10 shows a step in the assembly of the embodiment illustrated in FIG. 7.

As shown in FIG. 10, the rolled portion 60 can be rolled to a position shown at 66. As shown in FIG. 11, the securing member 64 may then be bent inwardly to a position shown at 68 to secure the bag 50 in a closed position for use.

A preferred embodiment of this invention has been disclosed, however, a worker of ordinary skill in the art would recognize a certain modification to come within the scope of this invention. For that reason, the following claims should be studied in order to determine the true scope and content of this invention.

I claim:

1. A bag assembly for receiving wastes from a patient through an opening in the patient comprising:

a bag for receiving and storing the waste having a selectively openable bottom which may be rolled to a closed position and secured at the closed position;

a patch positioned between the bag and a seal, the patch adhesively contacting the patient and surrounding the opening in the patient, the bag fixed relative to the patch;

the seal being fixed to the patch and disposed between the patient and the patch and defining an internal bore and having a substantially planar annular region extending beyond the patch pressing against the patient immediately around the opening in the patient;

an anti-back flow member received within the bag, and positioned within the bag and extending from the seal, the anti-back flow member being in the form of a thin plastic tube and being formed of thin plastic film, such that it presents little resistance to waste moving therethrough, the thin plastic tube having an internal diameter greater than the internal diameter of the bore through the seal and surrounding the bore, such that waste which moves from the opening in the patient through the seal and into the thin plastic tube tends not to contact the thin plastic tube adjacent the opening at the seal, the waste moves through the thin plastic tube and into the bag with moisture between sides of the tube from the waste passing therethrough causing sides of the tube to adhere to each other;

a flat spacer surrounding the anti-back flow member and also contacting the patch, the spacer supporting an entrance to both the bag and the anti-back flow member, the spacer defining belt loops positioned on each side of the bag;

a deformable member securing the rolled bag in the closed position; and a belt secured around the patient and engaging the belt loops to secure the bag on the patient.

* * * * *